United States Patent [19]

Iwamura

[11] 4,428,876

[45] Jan. 31, 1984

[54] PROCESS FOR ISOLATING SAPONINS AND FLAVONOIDS FROM LEGUMINOUS PLANTS

[75] Inventor: Junichi Iwamura, Kashiwara, Japan

[73] Assignee: Tokiwa Kanpo Pharmaceutical Co., Ltd., Japan

[21] Appl. No.: 505,566

[22] Filed: Jun. 17, 1983

[30] Foreign Application Priority Data

Aug. 19, 1982 [JP] Japan ............................ 57-144298

[51] Int. Cl.$^3$ .................... A23J 1/14; C07G 3/00; C08B 37/00
[52] U.S. Cl. ...................... 260/123.5; 260/112 R; 536/4.1; 536/4.4; 536/8; 536/128
[58] Field of Search ................. 260/123–125, 260/112 R; 536/4.1, 4.4, 8, 128

[56] References Cited

U.S. PATENT DOCUMENTS 2,681,907 6/1954 Wender ................................ 536/8
3,154,531 10/1964 Yoshimura et al. ............. 260/123.5

FOREIGN PATENT DOCUMENTS 3040246 5/1981 Fed. Rep. of Germany ....... 536/4.4

*Primary Examiner*—Howard E. Schain
*Attorney, Agent, or Firm*—Jones, Tullar & Cooper

[57] ABSTRACT

A process for isolating saponins and flavonoids from leguminous plant which comprises extracting a part or the whole of the said plant with an aqueous alkaline solution, separating the extract from insoluble matters comprising fibrous materials, applying the extract on non-polar or slightly polar adsorbent resin to adsorb the saponins and flavonoids on the said resin, and treating the resin with a polar solvent to elute the saponins and the flavonoids adsorbed on the said resin.

8 Claims, No Drawings

PROCESS FOR ISOLATING SAPONINS AND FLAVONOIDS FROM LEGUMINOUS PLANTS

The present invention relates to a process for isolating at least one of saponins and flavonoids from leguminous plants, more particularly, to a process for separating and isolating at least one of saponins and flavonoids by extraction of leguminous plants with an aqueous alkaline solution, preferably at room temperature, as an indispensable step, which is combined with adsorption-elution steps using non-polar or slightly polar adsorbent resins.

It is known that leguminous plants contain fibrous materials, flavonoids, saponins, saccharides and proteins as the main ingredients. Especially, the fibrous materials and proteins have been widely used in the field of food industry for a long time. Recently, medical use of flavonoids and saponins in soybeans has attracted special interest. It was proposed, for example, in Japanese Patent Publication (unexamined) Nos. 64000/1981, 73025/1981 and 160981/1981 that their isolation was carried out by extracting soybeans with a polar solvent under heating, concentrating the extract, re-extracting the concentrate with n-butanol and concentrating the obtained extract.

Noticing the fact that each of the said main ingredient of the leguminous plant has its usefulness, the inventors of the present invention have searched for a process in which the said main ingredients can be separated or isolated easily, safely and economically. As the result of extensive study, it has been discovered that the said process can be attained by extraction, preferably after defatting, of leguminous plants with an aqueous alkaline solution, preferably at room temperature, as an indispensable step, which is combined with adsorption-elution steps using non-polar or slightly polar adsorbent resins and appropriate eluents. The present invention has been completed on the basis of the above findings.

According to the present invention, there is provided a process for isolating saponins and flavonoids which comprises extracting a part or the whole of the said plant with an aqueous alkali solution, separating the extract from insoluble matters comprising fibrous materials, applying the extract on non-polar or slightly polar adsorbent resin to absorb the saponins and flavonoids on the said resin, and treating the resin with a polar solvent to elute the saponins and flavonoids adsorved on the said resin.

The said part and leguminous plant may be anyone of flower, flower bud, fruit, seed, stalk and leaf, xylem, root and rhizonme, root nodule, and the whole plant. They may also be green or dried. The part or the whole plant is usually grind into pieces, defatted, if appropriate, by extracting with organic solvent such as n-hexane under heating and submitted to further treatment after drying.

The said saponins includes glucosides consisting of sapogenin such as triterpenoids or steroids and saccharides such as glucose, arabinose, galactose or glucuronic acid. Typical examples of leguminous saponins are glycyrrhizin (glycyrrhetinic acid+glucuronic acid) contained in *Glycyrrhiza glabra*, soysaponin contained in soybean and alfalfasaponin contained in *Medicago sativa*.

In terms of the present invention, the term "flavonoids" means flavone, flavonol, flavanone, flavanol, isoflavone and their hydroxy, methoxy, methyl or methlenedioxy derivatives as well as their glucoside. Examples of such flavonoids include pratol (7-hydroxy-4'-methoxyflavone) contained in *Trifolium pratense*, acaciin (5,7-dihydroxy-4'-methoxyflavone (acacetin-7-rhamno-glucoside) and robinetin (7,3',4',5'-tetrahydroxyflavonol), both contained in *Robinia pseudo-acacia*, liquiritin (7,4'-dihydroxyflavanone (liquiritigenin)-glucoside) contained in *Glycyrrhiza glabra*, genistin (5,7,4'-trihydroxyisoflavone (genistein)glucoside) contained in *Genista tinctoria*, daidzin (7,4'-dihydroxyisoflavone (daidzein)-glucoside) and tatoin (5,4'-dihydroxy-8-methlisoflavone), both contained in soybean, $\phi$-baptigenin (7-hydroxy-3'4'-methylenedioxyisoflavone) contained in *Baptisia tinctoria* etc.

Preferably, the defatted and dried pieces of plant obtained above are extracted with an aqueous alkaline solution at room temperature (1°–35° C.) with or without stirring, and the extract, i.e. the aqueous alkaline solution which contains at least one of saponins and flavonoids originally contained in the said pieces, is separated from unextractable and insoluble matters comprising fibrous materials by filtration or centrifugation.

The obtained extract is applied on non-polar or slightly polar adsorbent resin as it is (alkaline) or after acidified. When the extract is acidified (preferably to weak acidic), proteins separate out and they are collected to recover by filtration or centrifugation before treatment with the adsorbent resin.

When the extract is contacted with the adsorbent resin, saponins and flavonoids contained in the extract are adsorbed on the said resin leaving the rest of the extract which may contain unadsorbed substances to flow out. These saponins and flavonoids are eluted by treating the said adsorbent resin with a polar solvent such as methanol or ethanol. The eluate is concentrated as needed and treated with an appropriate solvent such as acetone to separate saponins and flavonoids with each other, which are recovered.

The effluent containing saccharides which are not adsorbed on the adsorbent resin, is acidified (preferably to weak acidic) when the extract is not acidified before the treatment with the resin, and proteins separated out are collected. The mother liquor is concentrated to recover the saccharides. If the extract is acidified before the treatment with the adsorbent resin, the effluent is concentrated directly to recover the saccharides.

According to the invention, the extraction of the main ingredients other than the fibrous materials with the aqueous alkaline solution is carried out at room temperature. Accordingly, the extract step in the present invention has the advantage that the heat energy cost is reduced, the sealing of extraction vessel is not required, and the extraction procedure can be visually observed.

When the extraction is carried out under heating, as in the known technique, the fibrous materials in the plant is degraded to form colloidal substances, which not only inhibit the post-treatment of the extract, but also decrease the efficiency of the extraction by taking other ingredients therein.

The advantages in the present invention can be summaried as follows: (1) contrarily to the known extracting process using lower aliphatic alcohol, there is no fear of ignition and explosion, and hence no necessity of providing any special equipment for explosion proof, because water is used for extraction in the present invention. In addition, the production cost is significantly decreased because extracting agent is inexpensive; (2)

consumption of heat energy and deterioration of the product are extremely low because the extraction is carried out at room temperature (1°-35° C.); (3) steps for purification and concentration can be shortened, and consumption of extra solvent and extra heat energy, which was seen in the known process, is considerably decreased, and efficiency is notably improved; (4) since all the compounds contained in plant materials can be fractionated, the materials can be used with high utilization rate.

EXAMPLE 1

Using 1 liter portion of n-hexane, 100 g of powdered soybean was extracted twice for 1 hour with heating to defat the soybean. After drying, the defatted soybean was extracted with 1.5 liters of 0.4% aqueous sodium hydroxide solution at room temperature (1°-35° C.). The extract was filtered to separate and remove fibrous materials. The filtrate was acidified with acetic acid to weak acidic and allowed to stand for 1 hour. Precipitates were filtered and dried under reduced pressure below 60° C. to give 27.25 g of soybean protein.

The filtrate freed from the precipitates was treated with slightly polar adsorbent resin. Thus, 200 ml of slightly polar, acrylic ester based adsorbent resin was dispersed in 400 ml of water and packed into a column having an inner diameter of 30 mm. The said filtrate was injected at the upper end of the column and flowed at a rate of 10 ml/min, while adsorbance was effected. The column was washed with water until effluent was colorless to remove substances which were not adsorbed on the slightly polar adsorbent resin. The effluent was concentrated to solidification below 60° C. and the residue was dried below 60° C. to yield 26.5 g of grayish brown soybean carbohydrates. Then, 500 ml of methanol or aqueous methanol was injected at the upper end of the column of the slightly polar adsorbent resin and flowed at a rate of 30 ml/min, thereby eluting saponins and isoflavones adsorbed on the slightly polar synthetic resin. Termination of the elution was monitored with thin-layer chromatography (carrier: silica gel, 60; developing solvent: chloroform/methanol/water=6/4/1; detection: heating at 105° C. for 5 minutes after spraying 5% sulfuric acid). The obtained eluate was concentrated below 60° C. and the residue was dried at 60° C. under reduced pressure to yield 1.05 g of a yellowish brown mixture of soybean saponins and soybean isoflavones. The mixture was washed with 30 ml of acetone to separate acetone-soluble isoflavones from acetone-insoluble saponins yielding 0.70 g of crude isoflavones and 0.33 g of crude saponins.

A similar result was obtained when the above described process was carried out using 200 ml of non-polar, styrene-vinylbenzene based adsorbent resin in place of the slightly polar, acrylic ester based adsorbent resin.

EXAMPLE 2

Using 1 liter portion of n-hexane, 100 g of powdered soybean was extracted twice for 1 hour with heating to defat the soybean. After drying, the defatted soybean was extracted with 1.5 liters of 0.4% aqueous sodium hydroxide solution at room temperature (1°-35° C.). The extract was filtered to separate and remove fibrous materials.

The filtrate freed from the fibrous materials was treated with non-polar adsorbent resin. Thus, 200 ml of non-polar, styrene-vinylbenzene based adsorbent resin was dispersed in 400 ml of water and packed into a column having an inner diameter of 30 mm. The said filtrate was injected at the upper end of the column and flowed at a rate of 10 ml/min, while adsorbance was effected. The column was washed with water until effluent was colorless to remove substances which were not adsorbed on the non-polar adsorbent resin. The obtained effluent was acidified with acetic acid to weak acidic and allowed to stand for 1 hour. Precipitates were collected by centrifugation and dried under reduced pressure below 60° C. to give 16.70 g of soybean protein. The supernatant was concentrated to solidification below 60° C. and the residue was dried below 60° C. to yield 20.60 g of reddish brown soybean carbohydrates. Then, 500 ml of methanol or aqueous methanol was injected at the upper end of the column of the non-polar synthetic resin and flowed at a rate of 30 ml/min, thereby eluting saponins and isoflavones adsorbed on the non-polar synthetic resin. Termination of the elution was monitored with thin-layer chromatography (carrier: silica gel, 60; developing solvent: chloroform/methanol/water=6/4/1; detection: heating at 105° C. for 5 minutes after spraying 5% sulfuric acid). The obtained eluate was acidified with acetic acid to weak acidic and allowed to stand for 1 hour to separate insoluble materials, which were filtered off. The filtrate was concentrated below 60° C. and the residue was dried at 60° C. under reduced pressure to yield 2.32 g of a yellowish brown mixture of soybean saponins and soybean isoflavones. The mixture was washed with acetone to separate acetone-soluble isoflavones from acetone-insoluble saponins yielding 1.39 g of crude saponins and 0.70 g of crude isoflavones.

A similar result was obtained when the above described process for treating fiber-freed filtrate was carried out, replacing the non-polar, styrene-vinylbenzene based adsorbent resin with 200 ml of slightly polar, acrylic ester based adsorbent resin.

EXAMPLE 3

Using 1.5 liters of 0.4% aqueous sodium hydroxide solution, 100 g of finely cut licorice root (*Glycyrrhiza radix*) was extracted at room temperature (1°-35° C.). The extract was filtered to separate and remove fibrous materials.

The filtrate freed from fibrous materials was treated with non-polar adsorbent resin. Thus, 200 ml of non-polar, styrene-vinylbenzene based adsorbent resin was dispersed in 400 ml of water and packed into a column having an inner diameter of 30 mm. The said filtrate was injected at the upper end of the column and flowed at a rate of 10 ml/min, while adsorbance was effected. The column was washed with water until effluent was colorless to remove substances which were not adsorbed on the non-polar adsorbent resin. The obtained effluent was acidified with acetic acid to weak acidic and allowed to stand for 1 hour. Precipitates were filtered off. The filtrate was concentrated to solidification under reduced pressure below 60° C. and the residue was dried at 60° C. to give 12.30 g of brown colored licorice carbohydrates.

Then, 500 ml of methanol or aqueous methanol was injected at the upper end of the column of the non-polar synthetic resin and flowed at a rate of 30 ml/min, thereby eluting saponins and flavanone glycoside absorbed on the non-polar synthetic resin. Termination of the elution was monitored with thin-layer chromatography (carrier: silica gel 60; developing solvent: chloroform:methanol:water=6:4:1; detection: heating at 105° C. for 5 minutes after spraying 5% sulfuric acid). The obtained eluate was acidified with acetic acid to weak acidic and allowed to stand for 1 hour to separate insoluble materials, which were filtered off. The filtrate was concentrated below 60° C. and the residue was dried under reduced pressure at 60° C. to yield 19.31 g of a yellowish brown mixture of licorice saponin (glycyrrhizin) and licorice flavanone glycosides (liquiritin, isoliquiritin, etc.).

We claim:

1. A process for isolating saponins and flavonoids from leguminous plant which comprises extracting a part or the whole of the said plant with an aqueous alkaline solution, separating the extract from insoluble matters comprising fibrous materials, applying the extract on non-polar or slightly polar adsorbent resin to adsorb the saponins and flavonoids on the said resin, and treating the resin with a polar solvent to elute the saponins and the flavonoids adsorbed on the said resin.

2. The process according to claim 1, wherein the part or the whole of the reguminous plant is defatted before extracting.

3. The process according to claim 1, wherein the extract is deproteinized after extracting and before applying on the resin.

4. The process according to claim 1, wherein the said extract separated from insoluble matters is acidified and precipitates formed are collected to recover proteins.

5. The process according to claim 2, wherein saccharides are recovered from effluent containing substances unadsorbed on the adsorbent resin.

6. The process according to claim 1, wherein the said extract separated from insoluble matters is directly applied on adsorbent resin, effluent containing unadsorbed substances is acidified, and precipitates formed are collected to recover proteins.

7. The process according to claim 6, wherein saccharides are recovered from the acidic effluent separated from the precipitates.

8. The process according to claim 1, wherein the saponins and the flavonoids in the eluate which is obtained by treatment of the adsorbent resin with the polar solvent are separated and recovered by treatment with solvent.

* * * * *